United States Patent [19]
Bierman

[11] Patent Number: 6,117,163
[45] Date of Patent: *Sep. 12, 2000

[54] CATHETER SECUREMENT DEVICE

[75] Inventor: Steven F. Bierman, Del Mar, Calif.

[73] Assignee: Venetec International, Inc., Mission Viejo, Calif.

[*] Notice: This patent is subject to a terminal disclaimer.

[21] Appl. No.: 09/133,710

[22] Filed: Aug. 13, 1998

Related U.S. Application Data

[63] Continuation of application No. 08/689,314, Aug. 7, 1996, which is a continuation-in-part of application No. 08/512,082, Aug. 7, 1995, Pat. No. 5,637,098.

[51] Int. Cl.$^7$ .................................................. A61B 17/04
[52] U.S. Cl. .......................... 606/232; 604/180; 24/16 R
[58] Field of Search ........................... 606/232; 604/180, 604/264, 280, 179; 24/16 R, 17 AP

[56] References Cited

U.S. PATENT DOCUMENTS

| | | |
|---|---|---|
| 2,707,953 | 5/1955 | Ryan . |
| 3,046,984 | 7/1962 | Eby . |
| 3,059,645 | 10/1962 | Hasbrouck et al. . |
| 3,556,096 | 1/1971 | Fuller et al. ............................. 128/171 |
| 3,677,250 | 7/1972 | Thomas . |
| 3,973,565 | 8/1976 | Steer . |
| 4,020,835 | 5/1977 | Nordstrom et al. . |
| 4,057,066 | 11/1977 | Taylor . |
| 4,059,105 | 11/1977 | Cutruzzula et al. . |
| 4,133,307 | 1/1979 | Ness . |
| 4,142,527 | 3/1979 | Garcia . |
| 4,449,975 | 5/1984 | Perry . |
| 4,453,933 | 6/1984 | Speaker . |
| 4,516,293 | 5/1985 | Beran .......................................... 24/16 |
| 4,633,863 | 1/1987 | Filips et al. . |
| 4,650,473 | 3/1987 | Bartholomew et al. . |
| 4,711,636 | 12/1987 | Bierman . |
| 4,919,654 | 4/1990 | Kalt . |
| 4,950,285 | 8/1990 | Wilk . |
| 5,000,741 | 3/1991 | Kalt . |
| 5,037,397 | 8/1991 | Kalt et al. . |
| 5,073,170 | 12/1991 | Schneider . |
| 5,079,804 | 1/1992 | Gregurich et al. . |
| 5,098,399 | 3/1992 | Tollini . |
| 5,123,913 | 6/1992 | Wilk et al. . |
| 5,147,322 | 9/1992 | Bowen et al. . |
| 5,192,273 | 3/1993 | Bierman et al. . |
| 5,192,274 | 3/1993 | Bierman . |
| 5,195,981 | 3/1993 | Johnson . |
| 5,224,935 | 7/1993 | Hollands ................................. 604/180 |

(List continued on next page.)

FOREIGN PATENT DOCUMENTS

| | | |
|---|---|---|
| 0 274 418 A2 | 7/1988 | European Pat. Off. . |
| 0 470 709 A1 | 2/1992 | European Pat. Off. . |
| 31 10 023 A1 | 9/1982 | Germany . |
| 88 11 131 8 U | 2/1989 | Germany . |
| 2 219 034 | 11/1989 | United Kingdom . |
| WO 80/01458 | 7/1980 | WIPO . |
| WO 92/19309 | 11/1992 | WIPO . |

*Primary Examiner*—Michael Buiz
*Assistant Examiner*—Julian W. Woo
*Attorney, Agent, or Firm*—Knobbe Martens Olson & Bear, LLP

[57] ABSTRACT

An anchoring system includes a simply-structured suture-like device which permits a fluid tube or similar medical article to be easily attached to the patient without the use of needles and without suturing anything to the patient. The anchoring device desirably includes two threads or filaments and two corresponding receptacles. The filaments include protuberances which cooperate with apertures of the receptacles to permit easy insertion of the distal ends of the filaments into the receptacles, but inhibit retraction of the filament distal ends from the receptacles. A health care provider simply wraps the filament around the fluid tube or threads the filament through a suture hole in the medical article, and then threads the distal end of the filament through the receptacle aperture until the filament holds the medical article tightly against an anchor pad of the anchoring system. The anchor pad in turn includes an adhesive bottom surface which can be attached to the patient's skin.

20 Claims, 8 Drawing Sheets

U.S. PATENT DOCUMENTS

| | | |
|---|---|---|
| 5,266,401 | 11/1993 | Tollini . |
| 5,267,967 | 12/1993 | Schneider . |
| 5,282,463 | 2/1994 | Hammersly . |
| 5,292,312 | 3/1994 | Delk et al. . |
| 5,304,146 | 4/1994 | Johnson et al. . |
| 5,342,317 | 8/1994 | Claywell . |
| 5,354,282 | 10/1994 | Bierman . |
| 5,395,344 | 3/1995 | Beisang, III et al. . |
| 5,413,562 | 5/1995 | Swauger . |
| 5,443,460 | 8/1995 | Miklusek . |
| 5,456,671 | 10/1995 | Bierman . |
| 5,468,228 | 11/1995 | Gebert . |
| 5,468,230 | 11/1995 | Corn . |
| 5,468,231 | 11/1995 | Newman et al. . |
| 5,496,282 | 3/1996 | Militzer et al. . |
| B1 5,147,322 | 9/1992 | Bowen et al. . |

CATHETER SECUREMENT DEVICE

RELATED CASE

This application is a continuation of copending application Ser. No. 08/689,314, filed Aug. 7, 1996, which is an continuation-in-part of application Ser. No. 08/512,082, filed Aug. 7, 1995, now U.S. Pat. No. 5,637,098.

BACKGROUND OF THE INVENTION

1. Field of the Invention

The present invention relates to an anchoring system for anchoring medical article, such as, for example, catheters, fluid supply and drainage tubes, pacemaker and transducer wires and the like to a body of a patient.

2. Description of Related Art

It is very common in the treatment of patients to utilize intravenous (IV) catheters to introduce fluids and medications directly into the bloodstream. In many cases, and particularly with respect to cardiac therapy, the IV catheter is introduced into a central or larger vein located close to the patient's heart. A typical catheter utilized in connection with a central vein is referred to as a "central venous catheter" ("CVC"), while a venous catheter peripherally inserted into the central circulation through a vein in the arm is sometimes referred to as a "peripherally inserted central catheter" ("PICC").

In these cases, long-term IV infusion typically requires that the catheter remain in place for many days. In order to secure such a central venous catheter or other catheter types in position at the insertion site, the catheter often is provided with an integrated or movable, flexible clamp with winged extensions which are sutured to the patient's skin. In other applications, the flexible clamp is covered by a rigid fastener, which receives the catheter/clamp combination in a friction-fit manner. The rigid fastener and the flexible clamp have lateral, aligned holes in them which allow the combination to be sutured to the patient's skin. Although this technique securely attaches the central venous catheter to the patient, it obviously is painful and uncomfortable for the patient. This prior retention procedure also is time consuming and inconvenient, poses the risk of needle-stick to the health care provider, and risks suture-site infection to the patient. In addition, suture material grips tube and catheters poorly, and can cut through the winged extension of the catheter.

SUMMARY OF THE INVENTION

A need therefore exists for an anchoring system which quickly and securely attaches a catheter, tube, electrical wire or similar article to the skin of a patient, without suturing.

One aspect of the present invention involves an anchoring system for securing a portion of a medical article to the body of a patient. The anchoring system comprises a base coupled to an adhesive bottom surface. At least two filaments extend from the base. Each filament includes at least one protuberance that is positioned on the filament toward a distal end of the filament. At least two receptacles also are coupled to the base. Each receptacle is arranged so as to cooperate with at least one of the filaments. Each receptacle includes at least one aperture which receives the respective filament distal end and protuberance. The aperture cooperates with the protuberance to inhibit retraction of the filament distal end from the receptacle.

In accordance with another aspect of the present invention, an anchoring system is provided for securing a portion of a medical article to the body of a patient. The anchoring system comprises a base coupled to an anchor pad. The anchoring pad includes an adhesive bottom surface which is intended to be secured to the patient's skin. Means also are provided for securing the medical article to the base.

The present anchoring system also has utility in non-medical applications. For instance the anchoring system can be used, as explained below, to support and bundle wires, cables, tubes and other non-medical articles. Accordingly, an additional aspect of the present invention involves an anchoring system for securing a portion of an article to a support. The anchoring system comprises a base coupled to an adhesive bottom surface. An elongated thread extends from the base. A corresponding receptacle is also connected to the base at a position spaced from the thread. The receptacle is configured to receive at least a distal end of the thread with structure on the thread and receptacle interengaging. This interengaging structure of the thread and receptacle permits insertion of the thread's distal end into the receptacle but inhibits retraction of thread's distal end from the receptacle.

BRIEF DESCRIPTION OF THE DRAWINGS

These and other features of the invention will now be described with reference to the drawings of a preferred embodiment which is intended to illustrate and not to limit the invention, and in which.

DETAILED DESCRIPTION OF A PREFERRED EMBODIMENT

Figure 1:
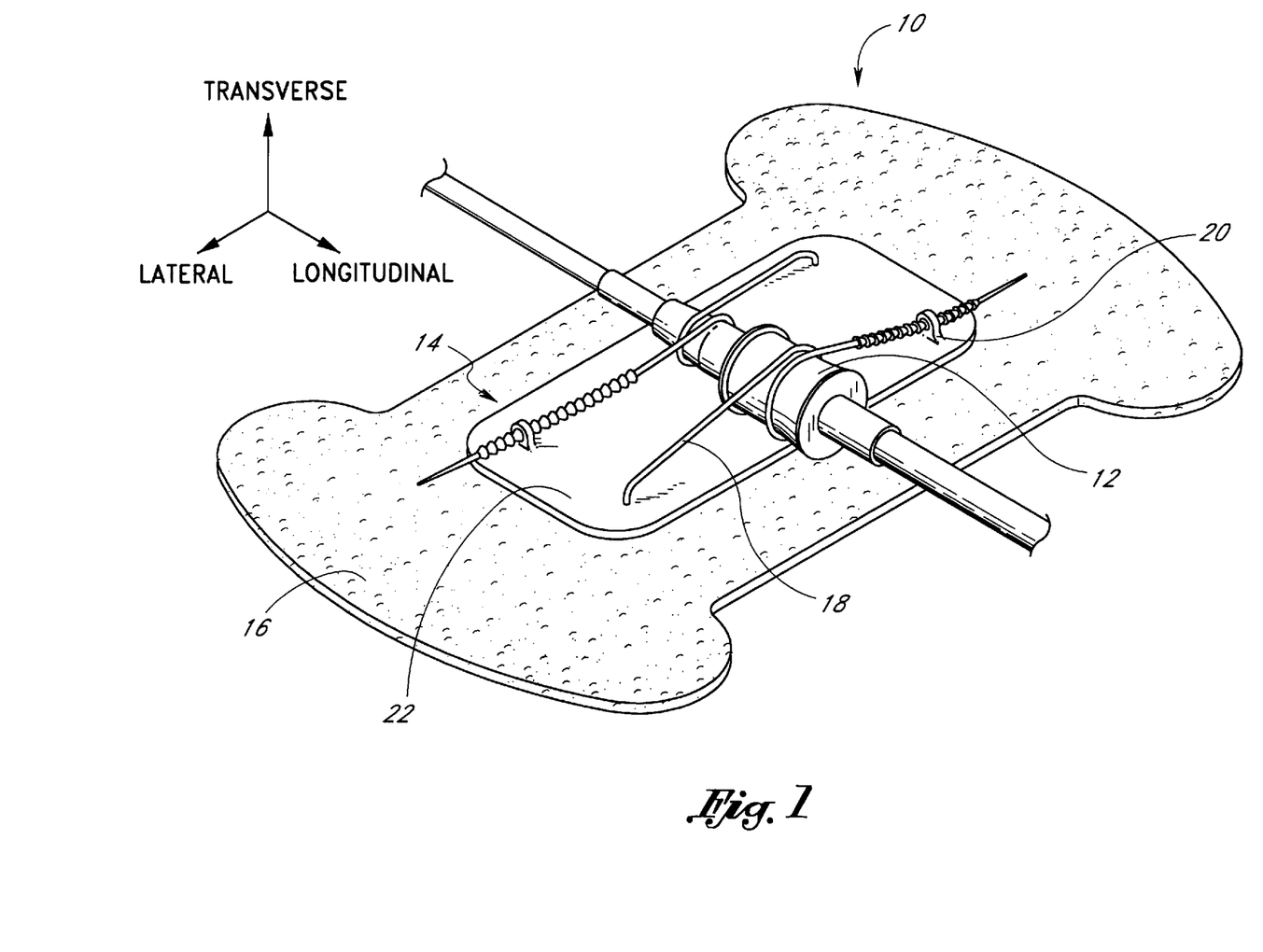
FIG. 1 is a perspective view of an anchoring system in accordance with a preferred embodiment of the present invention, together with an exemplary catheter and fluid tube coupling.

FIG. 1 illustrates an anchoring system 10 which is configured in accordance with a preferred embodiment of the present invention and is used in connection with a catheter-fluid line connector 12 (e.g., a luer-lock connector). It is understood, however, that the present anchoring system 10 also can be successfully utilized in connection with other types of medical articles, such as for example, but without limitation, CVCs, PICCs, Foley catheters, and hemodialyses catheters, surgical drainage tubes, feeding tubes, chest tubes, nasogastric tubes, as well as with electrical wires or cables connected to external or implanted electronic devices or sensors. Thus, as used herein, the term "medical article" is meant generically to include catheters, fluid supply and drainage lines, connectors, adaptors, electrical wires and cables, and the like, all of which may be retained by the present anchoring system 10. It therefore should be understood that the principles of the present invention are not limited to PICCs or central line catheters.

The present anchoring system 10 also can be used with non-medical articles as well. For instance, the anchoring system 10 can be used to secure wires, tubing, cables and like articles to a support (e.g., a wall, stud, pipe, etc.). It is appreciated that those skilled in the art can readily adapt the illustrated embodiments of the present invention to suit any of a variety of non-medical applications.

Figure 2:
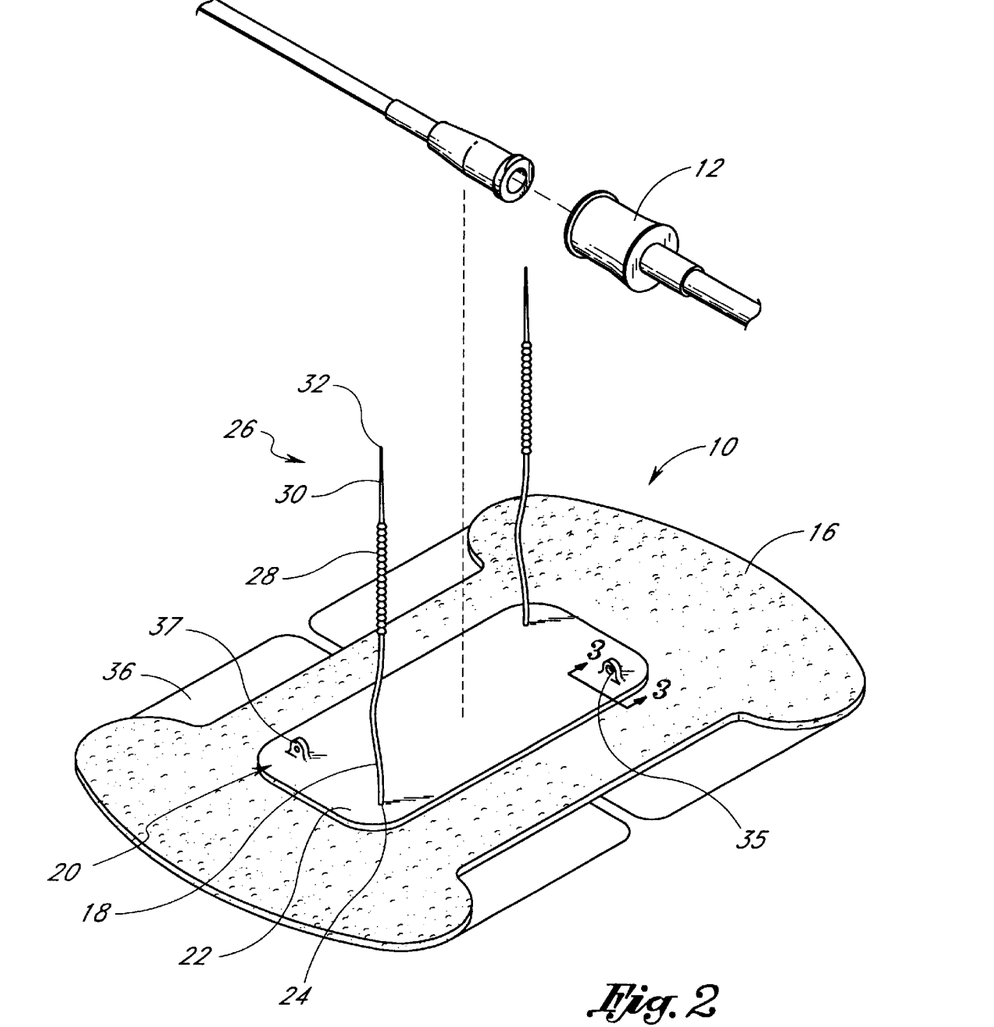
FIG. 2 is an exploded perspective view of the anchoring system and the catheter and fluid tube coupling of FIG. 1.

With reference to FIGS. 1 and 2, the anchoring system 10 includes a retention mechanism 14 mounted on top of an anchor pad 16. The anchor pad 16 includes a self-adhesive backing (not shown) to secure the retention mechanism 14 to the patient's skin. The retention mechanism 14 includes at least one filament or thread 18 which cooperates with a corresponding receptacle 20. By means of cooperation between the filament 18 and the receptacle 20, as described below in more detail, the connector 12 can be conveniently and painlessly anchored to and released from the patient's skin.

The individual components of the anchoring system 10 will now be described in detail. To assist in the description of the components of the anchoring system 10, a coordinate system has been provided. FIG. 1 illustrates a longitudinal axis, a transverse axis and a lateral axis in relation to the anchoring system 10. The longitudinal axis extends in a direction generally parallel to an axis of the tube. The lateral axis lies perpendicular to the longitudinal axis within the plane of the anchor pad 16. The transverse axis extends transverse to the longitudinal and lateral axes. Additionally, as used herein, the "longitudinal direction" refers to a direction substantially parallel to the longitudinal axis. "The lateral direction" and "the transverse direction" are in reference to the lateral axis and the transverse axis, respectively. The terms "proximal" and "distal" are also used to describe some of the components of the anchoring system 10. These terms are used in reference to the proximity of the base.

In the illustrated embodiment, the retention mechanism 14 includes a base 22 and a pair of filaments 18 that extend from the base 22. The retention mechanism 14 of course can include other numbers of filaments 18 in order to suit a specific application.

Each filament 18 includes a fixed proximal end 24, a free distal end 26 and at least one protuberance (generally indicated by reference numeral 28) positioned therebetween. The filaments 18 can have a variety of lengths depending upon the particular application of the anchoring device 10. For use with anchoring catheters and medical tubings, each filament 18 desirably has a length of about 5 inches; however, much longer or short lengths also are possible. The filaments 18 also can have a various diameter sizes depending upon the required strength of the filaments 18.

In the illustrated embodiment, each filament 18 includes a plurality of protuberances 28 arranged in series between the distal end 26 and the proximal end 24 of the filament 18. It is contemplated, however, that the filaments 18 can be configured to allow a health care provider to form the protuberance 28 in the filament 18 by tying a knot toward the distal end 26 of the filament 18.

As seen in FIG. 2, the protuberances 28 generally have identical barb-like shapes. In the illustrated embodiment, each protuberance 28 of the filament 18 has a generally conical shape with a maximum diameter at a proximal end of the protuberance 28. Although not illustrated, the protuberances 28 can take a variety of other shapes, such as for example, hollow conical shapes, arrow shapes, or transverse rib-like shapes. The proximal end of each protuberance 28, however, desirably has a diameter which is larger than the diameter of the filament 18. As such, in the illustrated embodiment, the proximal end of each protuberance 28 forms a flat surface that lies generally transverse to a longitudinal axis of the corresponding filament 18. The proximal end surface of some or all of the protuberances alternatively can slope or project toward the distal end of the filament 18.

The filament 18 desirably includes a needle-like shaped distal portion 30 with a generally pointed, but blunt end portion 32 positioned at the distal end of the filament 18. The distal portion 30 smoothly tapers with increasing diameter from the end 32 toward the distal-most protuberance 28. The diameter of the distal portion 30 at a point adjacent the distal-most protuberance 28 desirably equals the diameter of the filament 18 proximal to the protuberances 28.

The retention mechanism 14 also includes at least one and preferably a plurality of receptacles 20 positioned on the base 22. Each receptacle 20 is arranged on the base 22 to cooperate with at least one filament 18, as discussed below.

The receptacles 20 receive the distal ends 26 of the filaments 18 in a manner permitting the insertion of the filament 18 into the receptacle 20, but inhibiting the retraction of the filament 18 from the receptacle 20. For this purpose, the corresponding filament 18 and receptacle 20 include interengaging structure that allows the filament 18 to be easily inserted into the receptacle 20 in one direction with a first degree of force but prevents retraction of the filament 18 when a same or greater degree of force is applied to the filament 18 in the opposite direction. A larger degree of force is required to retract the filament 18 from the receptacle 20.

In the embodiment illustrated in FIGS. 1 and 2, the interengaging structure between the corresponding filament 18 and the receptacle 20 comprises the protuberances on the filaments 18 and apertures 34 of the receptacles 20. The interengaging structures of the filament-receptacle pairings are substantially identical, and the following description of one should be understood as applying equally to both, unless specified to the contrary.

Figure 3:
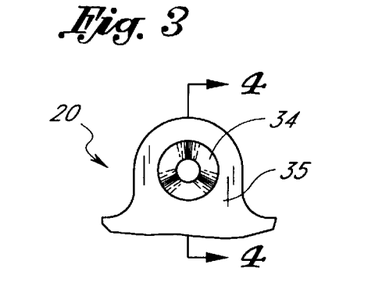
FIG. 3 is a side plane view of a receptacle of the anchoring system of FIG. 2 as viewed in the direction of line 3—3.
Figure 4:
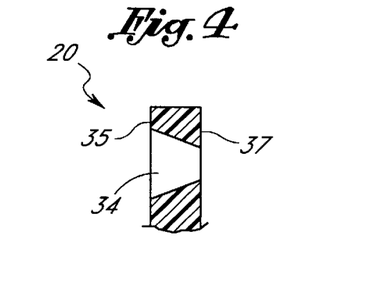
FIG. 4 is a cross-sectional view of the receptacle of FIG. 3 taken along line 4—4.

As best seen in FIGS. 3 and 4, each aperture 34 advantageously has a conical or funnel-like shape to help guide the distal end 32 of the filament distal portion 30 through the aperture 34. The aperture 34 tapers from a large diameter on an inner side 35 of the receptacle to a smaller diameter of the outer side 37 of the receptacle 34. The smaller diameter desirably is larger than the maximum diameter of the filament distal portion 30, but smaller than the maximum diameter of the protuberances 28.

Figure 5:
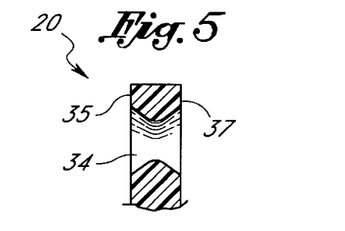
FIG. 5 is a cross-sectional view of a receptacle configured in accordance with another embodiment of the present invention.

The receptacle also can facilitate insertion from both sides of the receptacle, rather than the unidirectional configuration of the receptacle illustrated in FIG. 4. As seen in FIG. 5, the receptacle can have an hour-glass or double conical shape to help guide the distal end 32 of the filament through the aperture from either the inner side 35 or the outer side 37 of the receptacle 20. On each side of the aperture 34, the aperture 34 tapers from a larger diameter to a smaller diameter.

The smaller diameter section of the aperture occurs at the center of the receptacle's width, at a point equally distanced from the inner side 35 and the outer side 37 of the receptacle 20. The smaller diameter desirably is larger than the maximum diameter of the filament distal portion 30, but smaller than the maximum diameter of the protuberances 28. Because the aperture tapers to the small diameter from either side 35, 37 of the aperture, the filament 18 can be easily inserted into the double-conical aperture 34 from either side.

As common to the retention mechanism 14 which includes receptacles 20 configured in accordance with either of the embodiments illustrated in FIGS. 4 and 5, the receptacle 20 and/or the protuberances 28 of the associated filaments 18 are configured such that a wall of the receptacle 20 about the aperture 34 and/or the protuberances 28 deflect to allow the larger diameter protuberances 28 to pass through the smaller diameter aperture 34 of the receptacle 20. In the illustrated embodiment of FIG. 4, the thin wall about the aperture 34 at its outer side 37, the thin peripheral thickness of the protuberance 28 at its proximal end, and the elastic nature of the plastic from which these components are formed, provides the required deflection necessary for the protuberances 28 to pass through the aperture 34. Once the protuberance 28 passes through the small end of the aperture 34, the protuberance 28 and receptacle 20 spring back to inhibit retraction of the protuberance 28 through the aperture 34.

Figure 6:
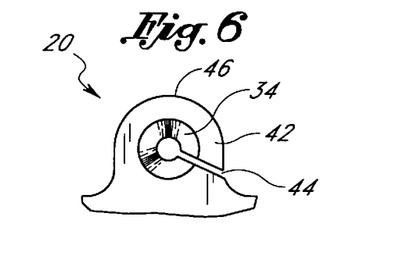
FIG. 6 is a side elevational view of a receptacle configured in accordance with an additional embodiment of the present invention.

The receptacles 20 can be configured to provide a convenient way to intentionally release the filament 18 from the receptacle 20. As seen in FIG. 6, the receptacle can include an opening or slit 44. The slit 44 extends from the outer perimeter 46 of the wall 42 to the aperture 34, and desirably slopes toward the base 22. The slit 44 has a gap spacing that is substantially smaller than the diameter of the aperture 34, and that is desirably smaller than a minimum diameter of the filament 18 (which occurs between adjacent protuberances 28).

The slit 44 in the wall of the receptacle 20 facilitates insertion of the filament 18 into the aperture 34 by providing flexibility to the receptacle wall 42 when the filament 18 is drawn through the aperture 34. The filament also can be removed from the aperture 34 by sliding a small diameter portion of the filament 18, which occurs between adjacent protuberances 28, into the slit 44. Further transverse movement (i.e., movement in a direction which is transverse to the direction of insertion into the receptacle 20) of the filament 18 slides the filament 18 out of the aperture 34 through the slit 44.

The configuration of the slit 44 requires that the transverse movement occur under a deliberate force. The small size of the slit 44 relative to the diameter of the filament 18, and the sharp transition edges between the diameter of the aperture 34 and the slit 44 mandate that a transverse force of sufficient strength to deflect the upper portion of the receptacle away the base 22, be applied in order to move the filament 18 in the transverse direction. In addition, the sloping orientation of the slit 44 toward the patient makes it unlikely that such a sufficient transverse force could be applied unintentionally. Rather, a health care provider must intentionally move the filament 18 in this direction through the slit 44.

With reference back to FIG. 1, each filament 18 and corresponding receptacle 20 are positioned on opposite sides of the base 22. In the illustrated embodiment, the filaments 18 also are positioned on opposite sides of the base 22 from each other, and the receptacles 20 are positioned on opposite sides of the base 22 from each other. The filaments 18 and the receptacles 20 advantageously are placed proximate to the corners of the base 22 with the filaments 18 positioned diagonally across the base 22 from each other and the receptacles 20 positioned diagonally across the base 22 from each other. The filaments 18 and receptacles 20 arranged accordingly define a space in which the catheter/fluid-line connector 12, a rigid fastener/flexible clamp combination (see FIG. 7), or similar medical article can be placed.

The base 22, filaments 18 and receptacles 20 of the retention mechanism 14 desirably are integrally formed together. This can be accomplished in any of a variety of ways which will be well known to one of skill in the art. For instance, the entire retention mechanism 14 can be integrally molded of plastic or nylon by injection molding.

With reference to FIG. 2, the retention mechanism 14 desirably is secured to the anchor pad 16 by means of a solvent bond adhesive. A suitable adhesive is available commercially from the Minnesota Mining and Manufacturing Company (3M), Part No. 4693.

The flexible anchor pad 16 comprises a layer of closed-cell, low-density polyethylene foam (LDPE) and a bottom adhesive mono-layer of medical-grade adhesive. The adhesive can be either diaphoretic or nondiaphoretic, depending upon the particular application. The foam layer with the adhesive bottom surface is available commercially from New Dimensions in Medicine of Columbus, Ohio. An upper surface of the foam layer is energized by corona treating the foam with a low electric charge, as known in the art. The corona-treated upper surface of the anchor pad 16 improves adhesion when attaching the retention mechanism 14 to the anchor pad 16.

A removable paper or plastic backing 36 desirably covers the bottom adhesive surface before use. The backing preferably resists tearing and is divided into a plurality of pieces to ease attachment of the pad 16 to the patient's skin. Desirably, the backing 36 is split along a center line of the flexible anchor pad 16 in order to expose only half of the adhesive bottom surface at one time. Although not illustrated, the backing 36 also advantageously can extend beyond at least one edge of the anchor pad 16 to ease removal of the backing from the adhesive layer. Such an extension of the backing 36 forms a tab which a health care provider can easily grip and remove while wearing protective gloves.

In operation, the health care provider initially selects a skin site on which the anchoring system 10 will be attached. For use with CVCs and PICCs, the anchoring system 10 desirably is applied to the skin of the patient in the vicinity of the catheter insertion site.

The health care provider cleanses and prepares the anticipated dressing site per hospital or agency protocol, usually using alcohol. The alcohol should be allowed to dry thoroughly. The health care provider then removes the anchor pad 16 from its packaging (not shown) and properly locates the pad 16 on the patient. The anchor pad 16 should be mounted on the patient so that the filaments 18 and the receptacles 20 are positioned on either side of the connector 12 or the catheter, and lie directly under the connector 12 or catheter.

The health care provider peels away the backing 36 from one half of the anchor pad 16 while pressing the exposed adhesive surface against the patient's skin. This process is repeated with the other half of the anchor pad 16. The pad 16 is pressed against the patient's skin to secure the anchor pad 16 to the patient. The health care provider is now ready to secure the tube connector 12 or catheter to the patient.

With reference to FIG. 1, which illustrates the securement of a fluid line connector 12, the first filament 18 is wrapped around one side of the connector 12 and is threaded through the opposing receptacle 20. As understood from FIG. 1, the filament 18 has a sufficiently long length to wrap around the connector 12 and easily threaded through the receptacle 20.

The distal end 26 of the filament 18 threads into the receptacle aperture 34 easily. The conical shape of the aperture 34 helps guide the distal portion 30 through the receptacle 20. The conical shape of the protuberances 28 further ease insertion of the filament 18 through the aperture 34, as described above. The flat proximal end of the protuberance 28, however, engages the outer surface 37 of the receptacles 20 and inhibits retraction of the filament 18 from the receptacle 20.

The health care provider likewise wraps the second filament 18 around the other side of the fluid line connector 12 and then inserts the distal end 26 into the opposing receptacle 20. The insertion process of the second filament 28 into the corresponding receptacle 20 is accomplished in the manner described above. The health care provider pulls both filaments 18 tight to draw the fluid line connector 12 against the base 22. Excess filament length can be severed or cut distal to the receptacle 20. The health care provider then can complete insertion site dressing per established hospital/agency dressing protocol.

The taut filaments 18 prevent the fluid line connector 12 from moving transversely away from the base 22 and from sliding either longitudinally or laterally over the base 22. In this manner, the anchoring system 10 assists maintaining the connection between the catheter and fluid line established by the connector 12.

It is also understood that the anchoring system 10 can be used to secure a variety of tubings or catheters, independent of a connector, to the patient. For instance, but without limitation, the securement device can be used with nasogastric tubes, Foley catheters, surgical drainage tubes, chest tubes and feeding tubes. In each of these applications, the filaments are wrapped around directly the tube or catheter and then inserted into the corresponding receptacle, as described above.

Figure 7:
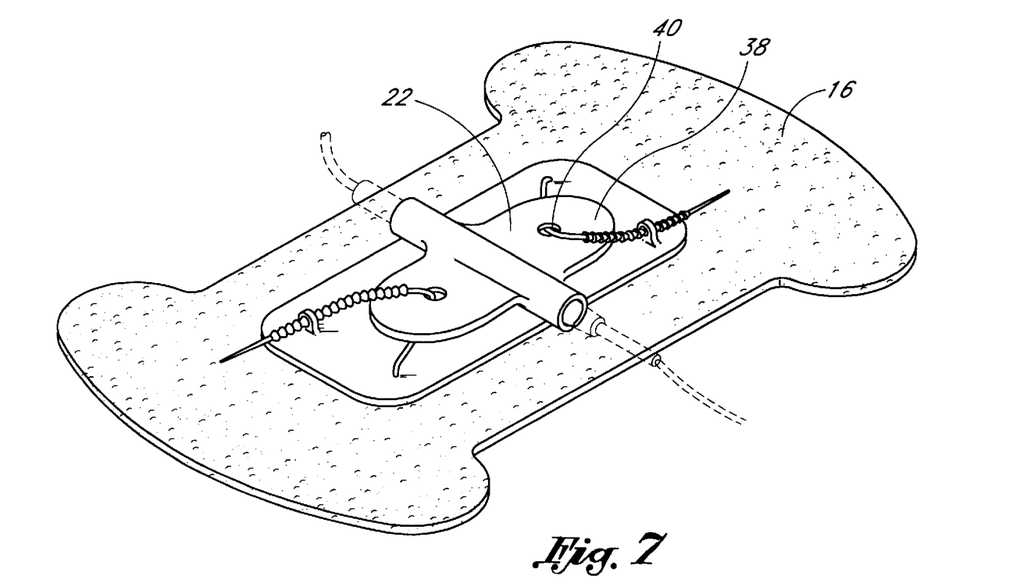
FIG. 7 is a perspective view of the anchoring system of FIG. 1 engaged with a conventional suture wing extension.

FIG. 7 also illustrates that the present anchoring system 10 can be used to secure to a patient a conventional clamp with suture wing extensions 38, such as, for example, that used with a Quinton® Hemodialysis catheter, a Cook® PICC, a steel needle, or a Huber® needle, a conventional rigid fastener/flexible clamp combination (see FIG. 10), such as, for example, that used with a Arrow® CVC, or another type suture seat, such as, for example, that used with the Baxter® Triple Lumen (not illustrated). If the catheter wings do not include suture holes, the health care provider can form holes in the winged extensions with a punch.

A health care provider places the suture wing extensions 38 on the base 22 between the filaments 18 and receptacles 20. One of the filaments 18 is threaded through the closest suture hole 40 of the suture wing and threaded through the adjacent receptacle 20. Likewise, the health care provider inserts the second filament 18 through the corresponding suture hole 40 and receptacle 20. The interengaging structures of the filaments 18 and the corresponding receptacles 20 prevent unintentional disengagement of the filaments 18 from the receptacles 20.

The anchoring system 10 additionally can be used with catheters including suture grooves. The health care provider wraps at least one of the filaments 18 around the groove which is provided on the catheter hub. The filaments 18 are then threaded through the opposite receptacles 20 and pulled taut. The health care provider completes the insertion site dressing in the manner described above.

These exemplary applications of the anchoring system 10 illustrate that each filament 18 can be inserted into either receptacle 20 to permit the anchoring system 10 to be used with more than one type of medical article. As shown in FIG. 1, when used with the opposing receptacle 20, the filament 18 can be wrapped around a portion of the medical article and threaded through the corresponding receptacle 20. And as shown in FIG. 7, when used with the adjacent receptacle 20, the filament 18 engages the structure on one side of the medical article and then can be threaded through the receptacle 20 on the same side of the retention mechanism 14. Other arrangements of the filaments 18 and receptacles 20 which will be readily apparent to those skilled in the art also are possible in order for the anchoring system 10 to be used with other types of medical articles.

When removal becomes necessary, the health care provider carefully removes any insertion site dressings which cover the anchoring system 10 and carefully snips the filaments 18 at a point between the proximal end 24 of the filament 18 and the corresponding receptacle 20 using a blunt hemostat. The medical article then can be lifted from the base 22 and the filaments 18 removed from the article. To remove the anchor pad 16, the health care provider lifts an edge of the pad 16 and gently strokes the undersurface with an alcohol swab while slowly but continuously lifting the edge. The anchor pad 16 can be peeled from the patient's skin in this manner. The health care provider then cleanses and prepares skin per hospital/agency protocol.

Thus, no painful or time-consuming sutures or other extensive procedures involving medial sharps (e.g., suture needles) are necessary to anchor a medical article to a patient's skin. In addition, the anchor pad 16 absorbs any forces which are incurred in the installation or removal of the anchoring system 10 and the medical device, thereby providing greater comfort for the patient.

Figure 8:
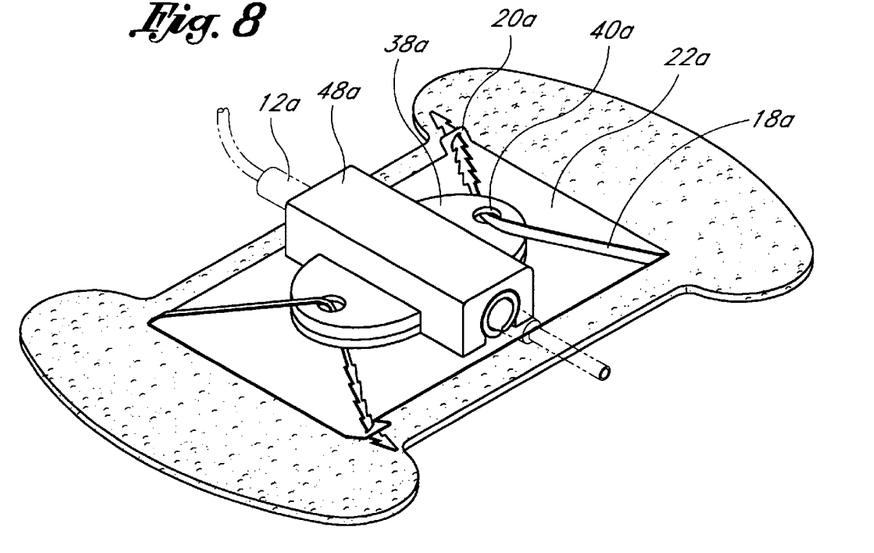
FIG. 8 is a perspective view of an anchoring system configured in accordance with another preferred embodiment of the present invention, illustrated in connection with an exemplary box-type clamp.
Figure 9:
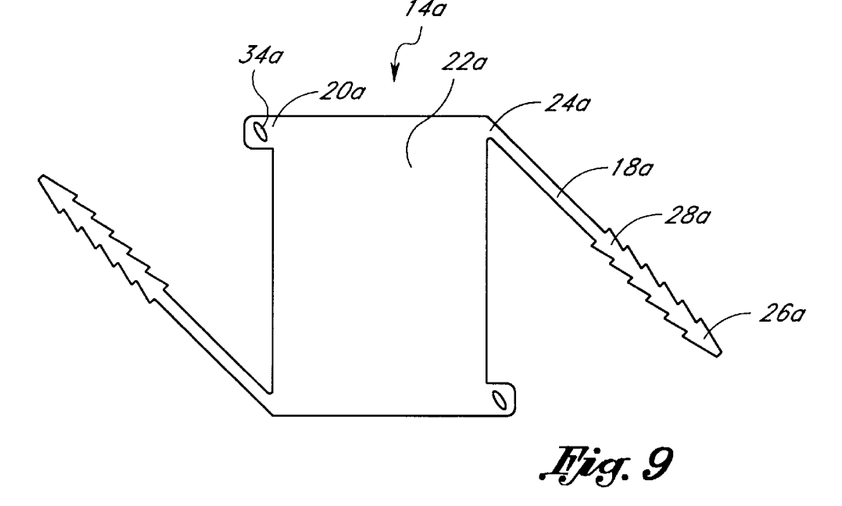
FIG. 9 is a top plan view of a retention mechanism of the anchoring system of FIG. 8.

FIGS. 8 and 9 illustrate an anchoring system configured in accordance with another preferred embodiment of the present invention. Only the construction of the retention mechanism of this embodiment differs from the above-described embodiment. Accordingly, the above description should apply equally to the embodiment of FIGS. 8 and 9, unless indicated otherwise. In addition, like reference numerals with an "a" suffix have been used to indicate like components between these embodiments to easy the reader's understanding.

The retention member 14a includes at least one filament 18a and at least one receptacle 20a which are attached to the base 22a. The filament 18a and corresponding receptacle 20a include interengaging structure which connects the filament 18a to the receptacle 20a when the filament 18a is drawn through the receptacle 20a. In the illustrated embodiment, the retention member 14a includes a two filament and receptacle pairings; however, the retention member 14a can include any number of pairings to suit a particular application.

The retention member 14a desirably is formed from a single flat sheet of material. Although the retention member 14a can be formed in a variety of way known to those skilled in the art, the retention member 14a desirably is die cut from a sheet of nylon. Other materials also can be used; however, the material should be sufficiently pliable to allow the filaments 18a and the receptacles 20a to be easily moved out of the plane of the base 22a in order to engage one another, and thus secure the medical device to the base 22a, in the manner described below.

As understood from FIG. 9, each filament 18a initially lies within the plane of the base 22a and is integrally formed with the base 22a. Likewise, each receptacle 20a initially lies within the plane of the base 22a and is integrally formed with the base 22a. In the illustrated embodiment, the filaments 18a are positioned across from each other at diagonal comers of the base 22a and the receptacles 20a also are position across from each other at diagonal comers of the base 22a. It will be appreciated, however, that the retention mechanism 14a can include other arrangements of the filaments 18a and the receptacles 20a on the base 22a.

Each filament 18a extends outwardly from the comer of the base 22a, but in a diagonal direction toward the end of the base 22a on which the corresponding receptacle 20a is positioned. The filament 18a has a fixed proximal end 24a (i.e., the end closest to the base 22a) and a free distal end 26a. A series of protuberances 28a are formed toward the distal end 26a. In the illustrated embodiment, the protuberances 28a are a plurality of barbs which lie in series. Except for the distal most barb, each barb 28a has truncated triangular shape. The distal-most barb 28a includes a tapered, blunt end 32a which helps guide the filament 18a into the corresponding receptacle 20a.

As seen in FIG. 8, each filaments 18a can be bent at its proximal end out of the plane of the base 22a. The filament 18a then can be extended to the corresponding receptacle 20a, as described below.

Each receptacle 20a includes an aperture 34a that receives the distal barbed portion of the corresponding filament 18a. For this purpose, the aperture 34a has a size larger than the distal end 26a of the filament 18a, but smaller than the maximum width of the barbs 28a. The barbs 28a consequently pass through the aperture 34a in a ratchet-like manner to inhibit retraction of the filament 18a from the receptacle 20a.

In the illustrated embodiment, each aperture 34a has an elliptical shape. The major axis of the aperture 34a generally lies parallel to an axis of the corresponding filament 18a. This orientation of the aperture 34a reduces filament twisting when inserted into the receptacle 20a.

Each receptacle 20a has a tab-like shape which can be bent out of the plane of the base 22a. The health care provider can easily insert the distal end 26a of the corresponding filament 18a into the aperture 34a with the receptacle 34a pulled away from the anchor pad 16a.

FIG. 8 illustrates an application of the present anchoring device with a conventional flexible clamp/rigid fastener combination ("a conventional catheter box clamp"). This application, however, is merely exemplary. The present anchoring system 10a can be used with any of a variety of medical device in the manner described above.

With reference to FIG. 8, the box clamp 48a having wing extensions 38a is placed generally at the center of the base 22a, between the filaments 18a and the receptacles 20a. One of the filaments 18a is threaded through the closest suture hole 40a of the clamp 48a and then is threaded through the adjacent receptacle 20a. Likewise, the second filament 18a is threaded through the corresponding suture hole 40a and receptacle 20a. The filaments 18a and the corresponding receptacles 20a engage with the barbs 28a ratcheting through the apertures 34a, to secure the catheter clamp 48a to the base 22a and to inhibit unintentional disengagement of the filaments 18a and the receptacles 20a.

FIGS. 10–14 illustrate an anchoring system configured in accordance with an additional preferred embodiment of the present invention. Again, only the construction of the retention member of this embodiment differs from the above-described embodiment of FIGS. 1–4. Accordingly, the above description should apply equally to the embodiment of FIGS. 10–14, unless indicated otherwise. In addition, like reference numerals with a "b" suffix are used to indicate like components between these embodiments to easy the reader's understanding.

Figure 10:
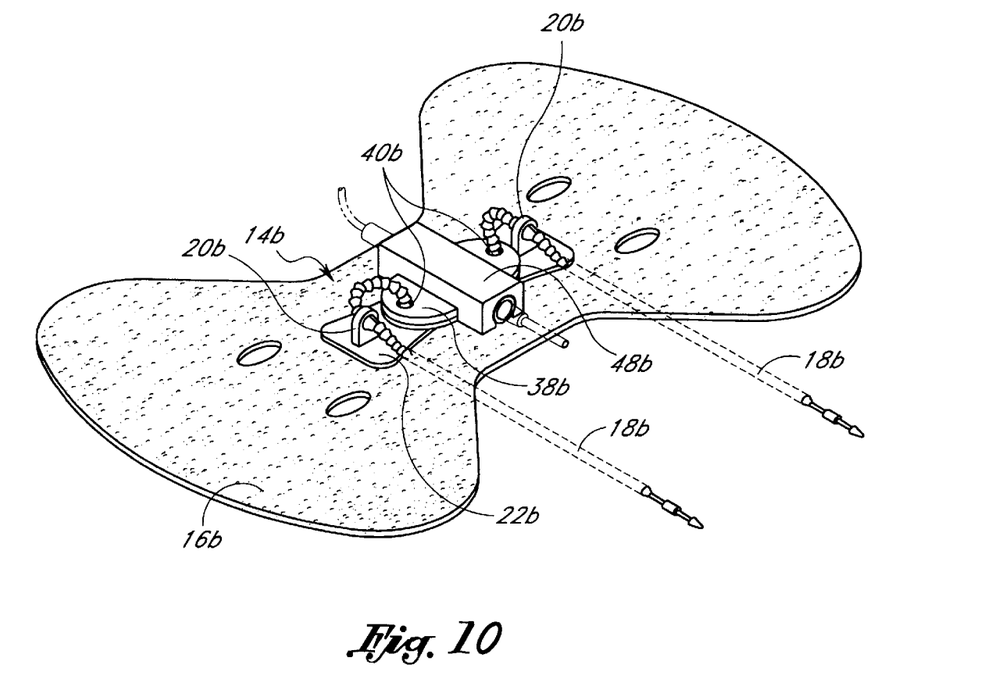
FIG. 10 is a perspective view of an anchoring system configured in accordance with an additional preferred embodiment of the present invention, illustrated in connection with an exemplary box-type clamp.
Figure 11:
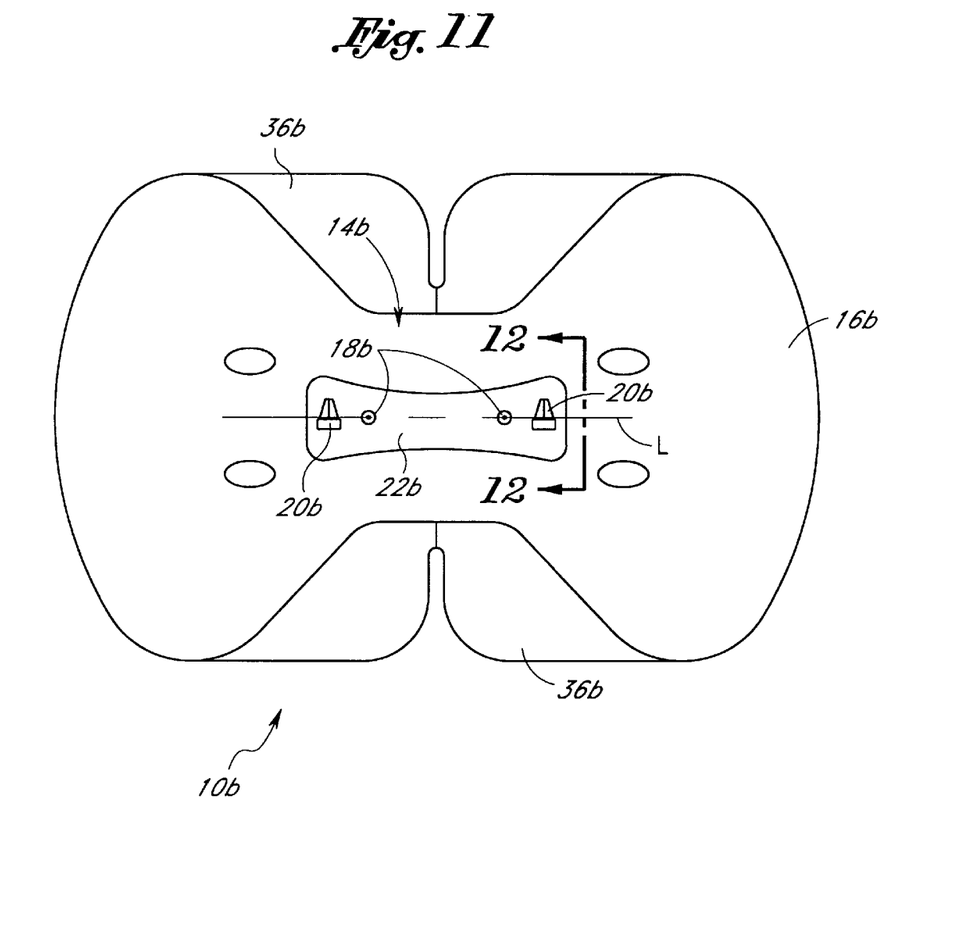
FIG. 11 is a top plan view of the anchoring system of FIG. 10, including a release layer attached to an adhesive pad of the anchoring system.

The retention mechanism 14b includes at least one filament or thread 18b which cooperates with a corresponding receptacle 20b. In the illustrated embodiment, the retention mechanism 14b includes a base 22b and a pair of filaments 18b that extend from the base 22b. The retention mechanism 14b of course can include other numbers of filaments 18b in order to suit a specific application. Each filament 18b includes a fixed proximal end 24b, a free distal end 26b and at least one protuberance (generally indicated by reference numeral 28b) positioned therebetween. In the illustrated embodiment, each filament 18b includes a plurality of protuberances 28b arranged in series between the distal end 26b and the proximal end 24b of the filament 18b.

Figure 12:
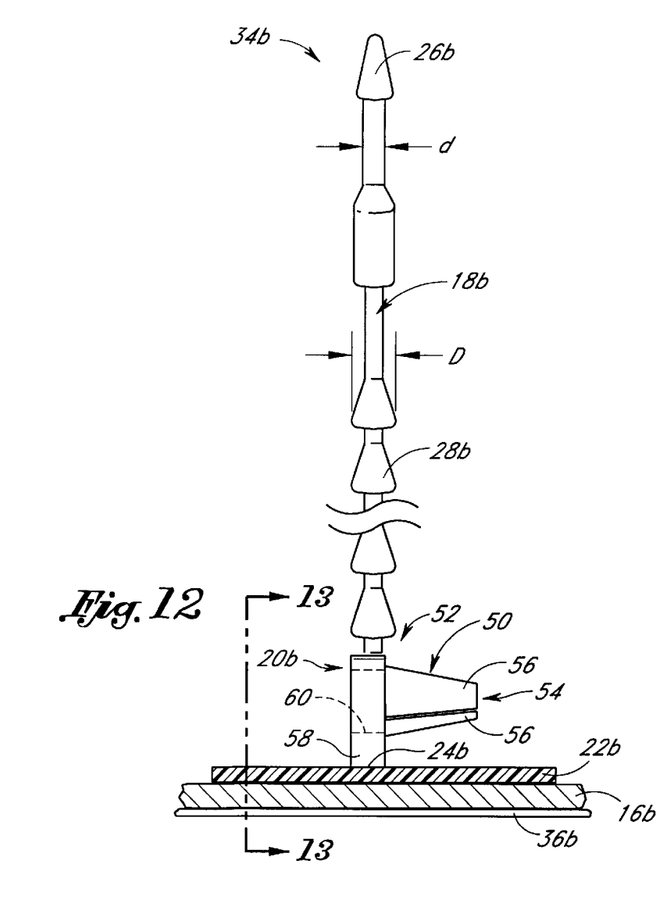
FIG. 12 is a partial cross-sectional, side elevational view of a retention mechanism and the adhesive pad of FIG. 11, taken along line 12—12.

As seen in FIG. 12, the protuberances 28b have identical barb-like shapes. In the illustrated embodiment, each protuberance 28b of the filament 18b has a generally conical shape with a maximum diameter D at a proximal end of the protuberance 28b. Although not illustrated, the protuberances 28b can take a variety of other shapes, such as for example, hollow conical shapes, arrow shapes, or transverse rib-like shapes. The proximal end of each protuberance 28b, however, desirably has a diameter D which is larger than a minimum diameter d of the filament 18b. As such, in the illustrated embodiment, the proximal end of each protuberance 28b forms a flat surface that lies generally transverse to a longitudinal axis of the corresponding filament 18b. The proximal end surface of some or all of the protuberances alternatively can slope or project toward the distal end of the filament 18b.

The filament 18b desirably includes a needle-like shaped distal portion 30b with a generally pointed, but blunt end 32b positioned at the distal end of the filament 18b. The needle-like shape of the distal end portion 30b tends to make the use of the filament 18b intuitive to a health care provider. The distal end portion 30b also is substantially rigid to ease insertion of the distal end 30b through the receptacle 20b.

As with the above-described embodiments, the filaments 18b can have a variety of lengths depending upon the particular application of the anchoring device 10b. For use with anchoring catheters and medical tubings, each filament 18b desirably has a length of about 5 inches; however, much longer or short lengths also are possible. The filaments 18b also can have a various diameter sizes depending upon the required strength of the filaments 18b.

The retention mechanism 14b also includes at least one and preferably a plurality of receptacles 20b positioned on the base 22b. Each receptacle 20b is arranged on the base 22b to cooperate with at least one filament 18b, as discussed below.

The receptacles 20b receive the distal ends 26b of the filaments 18b in a manner permitting the insertion of the filament 18b into the receptacle 20b, but inhibiting the retraction of the filament 18b from the receptacle 20b. For this purpose, the corresponding filament 18b and receptacle 20b include interengaging structure that allows the filament distal end 26b to be easily inserted into the receptacle 20 in one direction with a first degree of force but prevents retraction of the filament distal end 26b when a same or greater degree of force is applied to the filament 18b in the opposite direction. A larger degree of force is required to retract the filament 18b distal end from the receptacle 20b.

In the embodiment illustrated in FIGS. 10–14, the interengaging structure between the corresponding filament 18b and receptacle 20b comprises the protuberances 28b on the filament 18b and a trap device 50 of the receptacle 20b. Because the interengaging structure of the filament-receptacle pairings are substantially identical, the following description of one should be understood to apply equally to both, unless specified to the contrary.

Figure 13:
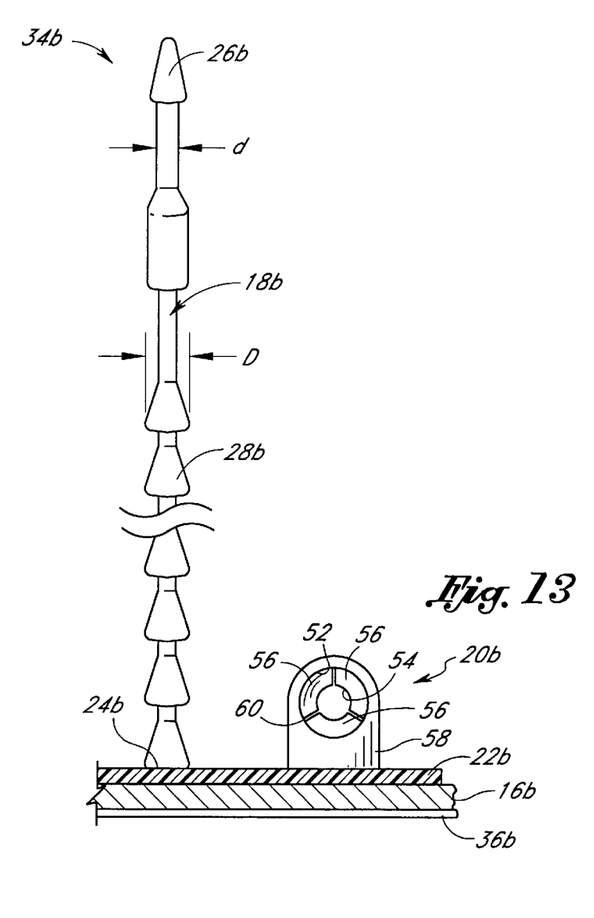
FIG. 13 is a partial cross-sectional front elevational view of the retention mechanism and adhesive pad of FIG. 12, taken along line 13—13.
Figure 14:
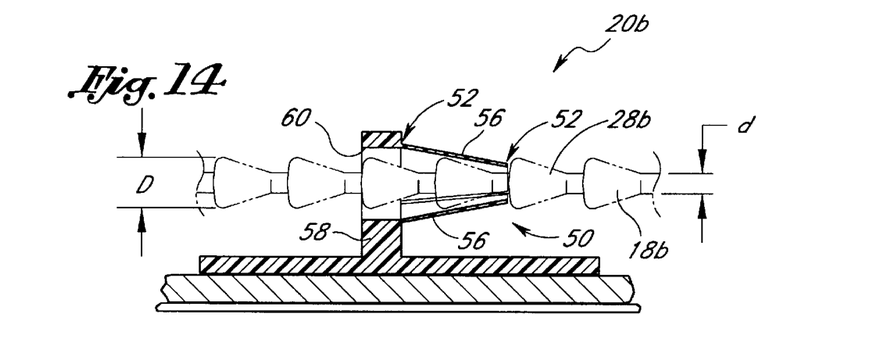
FIG. 14 is a cross-sectional view of a receptacle of the retention member of FIG. 12 with a portion of a filament of the retention member inserted into the receptacle.

As best seen in FIGS. 12–14, each trap device 50 has a conical or funnel-like shape to help guide the distal end 26b of the filament 18b into the trap device 50. Trap device 50 tapers from a large diameter 52 on one side of the receptacle 20b to a smaller diameter 54 on the other side of the receptacle 20b. The large diameter 52 is larger than the maximum diameter of the filament 18b (i.e., the maximum diameter of the protuberances 28b). The smaller diameter 54 desirably is smaller than the tip 32b of the filament distal end 26b to facilitate insertion of the filament 18b through the trap device 50. The smaller diameter 54, however, is smaller than the maximum diameter of the protuberances 28b, which in the illustrated embodiment, occurs at the proximal ends of the protuberances 28b.

The trap device 50 is formed by a plurality of flexible fingers 56. In the illustrated embodiment, three fingers 56 form the trap device 50. The fingers 56 extend from a lug 58 of the receptacle 20b at positions about the periphery of an aperture 60 through the lug 58. The fingers 56 converge toward the smaller diameter end 54 of the trap device 50.

As best seen in FIGS. 12 and 13, gaps exists between the fingers 56. These gap spacings are smaller than a minimum diameter d of the filament 18b, which in the illustrated embodiment occurs between the protuberances 28b.

The gap spacings allow the fingers 56 to deflect in the radial direction away from the insertion axis through the trap device 50. As seen in FIG. 14, the protuberance 28b forces the fingers 56 apart as it passes through the trap device 50. Once the protuberance 28b has passed through the smaller diameter end 54 of the trap device 50, the fingers 56 spring back to a diameter that is smaller than the diameter D of the flat proximal end of the protuberance 28b. In this manner, the cooperation between the trap device 50 and the protuberances 28b allows insertion of the filament 18b through the receptacle 20b in one direction, but inhibits retraction of the filament 18b.

In the illustrated embodiment, the trap devices 50 of the receptacles 20b face in the same direction. This arrangement simplifies the manufacture of the retention mechanism 14. It is understood, however, that the trap devices 50 can face in opposite directions in order to suit specific applications.

Figure 15:
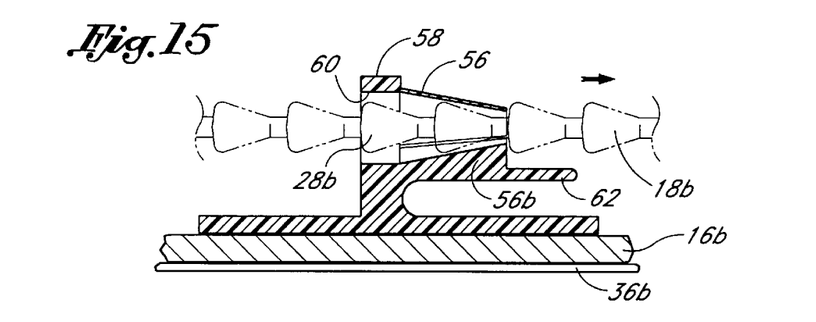
FIG. 15 is a cross-sectional view of another embodiment of a receptacle which can be used with the anchoring system, such as that illustrated of FIG. 10.
Figure 16:
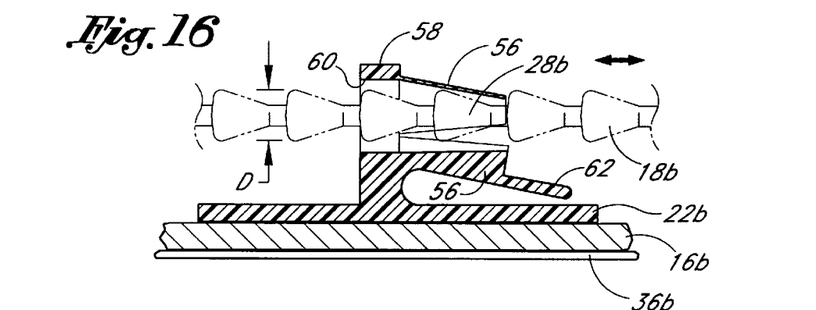
FIG. 16 is a cross-sectional view of the receptacle of FIG. 16 with a tang member of the receptacle deflected.

It may be advantageous in some applications to intentionally retract the filament 18b from the receptacle 20b. For this purpose, a release mechanism can be employed with the trap device 50 in order to disengage the trap device 50 from the protuberances 28b. FIGS. 15 and 16 illustrate an exemplary release mechanism.

As seen in FIG. 15, the finger 56 near the base 22b includes tab 62. The tab 62 desirably extends laterally to both sides of the receptacle 20b to ease manipulation of the tap 62. With this configuration, a health care provider can place one finger on one side of the filament 18b and another finger on the opposite side of the filament 18b and depress the tap 62.

FIG. 16 illustrates the tab 62 when depressed. The smaller end opening 52 enlarges with the tab 62 depressed to a size larger than the maximum diameter D of the protuberance 28b. The health care provider thus can withdraw the filament 18b from the trap device 50 with the release mechanism actuated in this manner.

Figure 17:
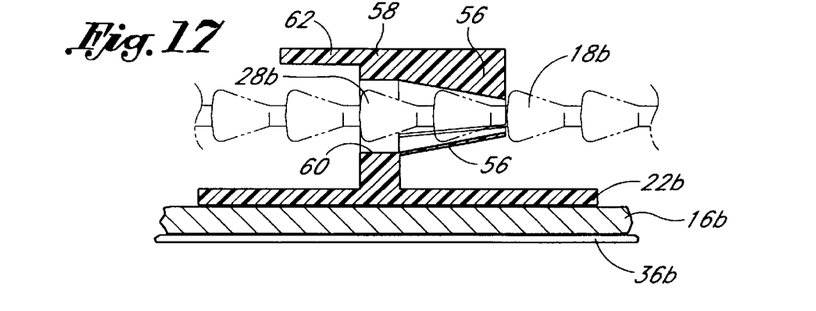
FIG. 17 is a cross-sectional view of an additional embodiment of a receptacle which can be used with an anchoring system, such as that illustrated in FIG. 10.

FIG. 17 illustrates another embodiment of the release mechanism with the tab 62 positioned on the upper side of the retainer lug 58. Downward deflection of the tab 56 causes the upper finger 56 to rise up. The smaller end opening 56 consequently enlarges to a size which facilitates retraction of the filament 18b, as described above.

With reference back to FIG. 11, the receptacles 20b and the filaments 18b desirably lie along a common line L, preferably along a center line of the base 22b in the lateral direction. This arrangement facilitates manufacture of the retention mechanism 14b by injection molding and allows the part to be made within only a two piece mold (which is significantly less expensive than multiple piece molds). In the illustrated embodiment, the base 22b has a generally rectangular shape with the long sides of the base 22b being concave. The filaments 18b lie inside the receptacles 20b and are spaced apart by a distance sufficient to receive the particular medical article to be anchored (e.g., a box clamp as illustrated in FIG. 10). The spacing between the filaments 18b of course can vary depending upon the particular article which the anchoring device 10b is designed to be used.

The retention mechanism 14b desirably is formed of a material having suitable flexibility to allow for the above-described operation of the trap device 50, as well as for the above-described operation of the release mechanism, should the retention mechanism 14b include such a mechanism. It also is desired that the retention mechanism 14b be injected molded in order to reduce fabrication costs. For these purposes, the retention mechanism 14b desirably is molded of a super tough nylon, such as that available commercially from DuPont, Part No. SP801, or of a polypropylene.

The retention mechanism 14b desirably is secured to the anchor pad 16b by means of a solvent bond adhesive. A suitable adhesive is available commercially from the Minnesota Mining and Manufacturing Company (3M), Part No. 4693.

The flexible anchor pad 16b comprises a layer of closed-cell, low-density polyethylene foam (LDPE) and a bottom adhesive mono-layer of medical-grade adhesive. The adhesive can be either diaphoretic or nondiaphoretic, depending upon the particular application. The foam layer with the adhesive bottom surface is available commercially from New Dimensions in Medicine of Columbus, Ohio. An upper surface of the foam layer is energized by corona treating the foam with a low electric charge, as known in the art. The corona-treated upper surface of the anchor pad 16b improves adhesion when attaching the retention mechanism 14b to the anchor pad 16b. A releasible backing, such as that described above, desirably covers the adhesive layer of the anchor pad 16b before application.

As common to each of the above-described anchoring systems, the present invention provides a sterile, tight-gripping, needle-free way to secure medical articles to a patient. The anchoring system thus eliminates accidental needle sticks and suture wound site infections and scarring because sutures are not required. In addition, the anchoring system can be used with any of a wide variety of catheters, tubes, wires, and other medical articles to provide universal securement using one style of securement device. Also, patient comfort enhances and application time decreases with the use of the present anchoring system.

As mentioned above, the present anchoring system also can be used in non-medical applications. In such applications, the anchoring system can secure items such as, for example, electrical wires, tubing, cables, etc., to a support structure. In this application, the components of the anchoring device need not be made of medical-grade materials. For instance, an adhesive tape (e.g., conventional duct tape) can replace the adhesive pad described above. The retention mechanism can be applied directly to the non-adhesive side of the tape. The adhesive surface of the tape is intended to secure the retention mechanism to the support.

Although this invention has been described in terms of a certain preferred embodiment, other embodiments apparent to those of ordinary skill in the art are also within the scope of this invention. Accordingly, the scope of the invention is intended to be defined only by the claims which follow.

What is claimed is:

1. An anchoring system for securing a portion of a medical article to the body of a patient, said anchoring system comprising a base coupled to an anchor pad having an adhesive bottom surface, at least two filaments extending from the base, and a plurality of sets of interengaging structures, each set of interengaging structures operating between the base and one of the filaments to secure a portion of the respective filament to the base, the filaments and the interengaging structures being unitarily formed with the base.

2. An anchoring system as in claim 1, wherein the sets of interengaging structures are spaced apart from each other on of the base.

3. An anchoring system as in claim 1, wherein the anchor pad includes a foam layer with a corona treated upper surface.

4. An anchoring system as in claim 1, wherein a solvent bond adhesive secures the base to the anchor pad.

5. An anchoring system as in claim 1, wherein each set of the plurality of interengaging structures comprises at least one protuberance disposed on the respective filament and a corresponding receptacle disposed on the base.

6. An anchoring system as in claim 5, wherein the receptacle is configured to receive a section of the filament.

7. An anchoring system as in claim 6, wherein the receptacle is further configured to inhibit retraction of the received filament section from the receptacle.

8. An anchoring system as in claim 7, wherein the receptacle is further configured to releasably receive the section of filament.

9. An anchoring system as in claim 5, wherein the interengaging structures comprise a plurality of protuberances disposed along a section of the respective filament.

10. An anchoring system for securing a portion of an article to a support, the anchoring system comprising a base coupled to a bottom adhesive, at least two elongated filaments, each filament having a distal end and proximal end being affixed to the base, and means for securing the distal end of at least one of the filaments to the base, said means being disposed at least in part upon said at least one filament.

11. An anchoring system as in claim 10, wherein said means further releasably secures the distal end of the one filament to the base, whereby the distal end can be intentionally released from the base.

12. An anchoring system as in claim 10 additionally comprising another means for securing the distal end of a corresponding filament to the base.

13. An anchoring system as in claim 12, wherein a point where the means secures the distal end of the respective filament to the base is spaced apart from the proximal end of the respective filament.

14. An anchoring system as in claim 10 additionally comprising an anchor pad having an upper side and a lower side, the base being attached to the upper side and the bottom adhesive covering at least a portion of the lower side of the anchor pad.

15. An anchoring system as in claim 10, wherein the means for securing the distal end of at least one of the filaments to the base, the filaments, and the base are unitarily formed together.

16. An anchoring system for securing a portion of an article to a support, the anchoring system comprising a base coupled to an adhesive bottom surface, an elongated filament projecting from the base and including a proximal end affixed to the base and a distal end, a receptacle disposed on the base apart from the proximal end of the filament, the receptacle being configured to receive at least the distal end of the filament, and coupling means for permitting the insertion of the filament distal end into the receptacle but inhibiting unintentional retraction of the filament distal end from the receptacle, said coupling means disposed at least in part upon the filament.

17. An anchoring system as in claim 16, wherein said means further releaseably secures the distal end of the one filament to the receptacle, whereby the distal end can be intentionally released from the receptacle.

18. An anchoring system as in claim 16 additionally comprising a second filament having a distal end, a second receptacle spaced apart from the second filament, and a second coupling means for permitting the insertion of the distal end of the second filament into the second receptacle but inhibiting unintentional retraction of the distal end from the second receptacle.

19. An anchoring system as in claim 16 additionally comprising an anchor pad having an upper side and a lower side, the base being attached to the upper side and the bottom adhesive covering at least a portion of the lower side of the anchor pad.

20. An anchoring system as in claim 16, wherein the base, filament, receptacle and coupling means are unitarily formed together.

* * * * *